US00PP08681P

United States Patent [19]

Austin

[11] Patent Number: Plant 8,681

[45] Date of Patent: Apr. 12, 1994

[54] ROSE PLANT 'AUSGLOBE'

[75] Inventor: David C. H. Austin, Albrighton, England

[73] Assignee: David Austin Roses Limited, Albrighton, England

[21] Appl. No.: 954,963

[22] Filed: Sep. 30, 1992

[51] Int. Cl.[5] ..... A01H 5/00

[52] U.S. Cl. ..... Plt./1

[58] Field of Search ..... Plt. 1, 26

*Primary Examiner*—Howard J. Locker
*Assistant Examiner*—E. F. McElwain
*Attorney, Agent, or Firm*—Klarquist, Sparkman, Campbell, Leigh and Whinston

[57] ABSTRACT

A bush rose variety having very large, soft pink flowers, branching habit, and strong fragrance.

1 Drawing Sheet

The present invention relates to a new and distinct variety of shrub rose plant of the Rosa hybrida class which was originated by me by crossing the variety Charles Austin, with an unnamed seedling.

The primary objective of this breeding was to produce a new rose variety having pink, quartered, scented flowers on a bushy plant which repeatedly flowers. The objective was substantially achieved along with other desirable improvements as evidenced by the following unique combination of characteristics which are outstanding in the new variety and which distinguish it from its parents, as well as from all other varieties of which I am aware:

1. Very large, soft pink flowers;
2. Branching habit; and
3. Strong fragrance.

Asexual reproduction of this new variety by budding, as performed at Albrighton, Wolverhampton, England, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Methuen Handbook of Colour, except where ordinary dictionary significance of color is indicated.

Parentage:

*Seed parent.*—Charles Austin.

*Pollen parent.*—An unnamed seedling.

Classification:

*Botanical.*—Rosa hybrida.

*Commercial.*—Shrub.

FLOWER

Observations made from specimens grown in a garden environment at in Albrighton, Wolverhampton, England in August, 1991.

Blooming habit: Recurrent.

Bud:

*Size.*—¾" long when the petals start to unfurl.

*Form.*—The bud form is globular with cuspidate apex.

*Color.*—When sepals first divide, the bud color is Violet brown 11E-F8. When half blown, the upper and lower sides of the petals are pale red 8A3 at top and salmon/peach 6A4/7A4 in center.

*Sepals.*—Color: Deep green 29E8 with Violet brown 11E8 pigmentation. Surface texture: Leathery. There are three lightly appendaged sepals. There are two unappendaged sepals with hairy edges.

*Receptacle.*—Color: Deep green 29D8. Shape: Goblet shaped. Size: Small, about ⅜"×¼". Surface: Smooth.

*Peduncle.*—Length: 1¼-2½". Surface: Smooth, glandular (sparse). Color: Medium green 29D8 with violet brown 10E6 blush. Strength: Bending.

Bloom:

*Size.*—Large. Average open size is 3½" in diameter.

*Borne.*—Singly, several together (1 to 5). If in clusters: irregular shape.

*Stems.*—Medium. Average length is 24 to 30 inches.

*Form.*—When first open: Cupped. Permanence: Flattens, outer petals curl back.

*Petalage.*—Number of petals under normal conditions: 45.

*Color.*—The upper side of the petals is pale red 12A3 (top) and 9A3 (center). The reverse side of the petals is the same. The base of petals has yellow 3A7 tip. The major color on the upper side is pale red 12A3.

*Variegations.*—None.

*Discoloration.*—The general tonality at the end of the first day: Slightly paler. At the end of the third day, the color of the majority of the petals is pinkish white 13A2 to reddish white 9A2.

*Fragrance.*—Strong, tea rose with citrus scent.

Petals:

*Texture.*—Thin, silky.

*Shape.*—Heart-shaped to round, apex is notched.

*Form.*—Cupped, edges slightly curved.

*Arrangement.*—Informal, with many petaloids in the center.

*Persistence.*—Petals drop off cleanly before drying.

*Lastingness.*—On the plant: Very long, 7 to 10 days. As a cut flower: Long, 5 to 7 days.

Reproductive parts:

*Anthers.*—Size: Medium. Quantity: Many. Color: Yellow. Arrangement: Partly tucked in calyx, mixed with petaloids.

*Filaments.*—Color: Orange 6A7.

*Pollen.*—Color: Gold yellow.

*Styles.*—Color: Pale green 30A2, Cerise 12C8 top.

*Stigmas.*—Color: Light yellow 4A4.

Form: Shrub.

Growth: Medium, branching.

Height: 42 to 48 inches.

Foliage: Number of leaflets on normal mid-stem leaves: 5.

*Size.*—Medium, 1¾"-2¾"×1-2" wide.

*Quantity.*—Normal.

*Color.*—New foliage: Dark green 28F8. Old foliage: Dark green 29F6 plus extensive Violet brown blush 10F6.

Leaflets:

*Shape.*—Base is round, pointed oval, cuspidate apex.

*Texture.*—Upper side: Leathery.

*Edge.*—Serrated.

*Serration.*—Double, small.

*Petiole rachis.*—Color: Dark green 29F8, with Violet brown blush 10F8.

*Petiole underside.*—With prickles, 0-2 per internode.

*Stipules.*—Medium, ¾-1" long.

*Disease resistance.*—Resistant to mildew and blackspot under normal growing conditions at Albrighton, Wolverhampton, England.

Wood:

*New wood.*—Color: Reddish, dark brown 9F6.

*Old wood.*—Color: Dark green 29F6. Bark: Smooth.

Prickles:

*Quantity.*—On main canes from base: Few. On laterals from main canes: Few.

*Form.*—Medium, straight.

*Color when young.*—Red, violet brown 10E8.

*Position.*—Evenly distributed.

Small prickles:

*Quantity.*—On main stalks: None. On laterals: None.

I claim:

1. A new and distinct variety of rose plant of the rosa hybrida class, substantially as herein shown and described, characterized particularly as to novelty by the unique combination of its very large, soft pink flowers, branching habit, and strong fragrance.

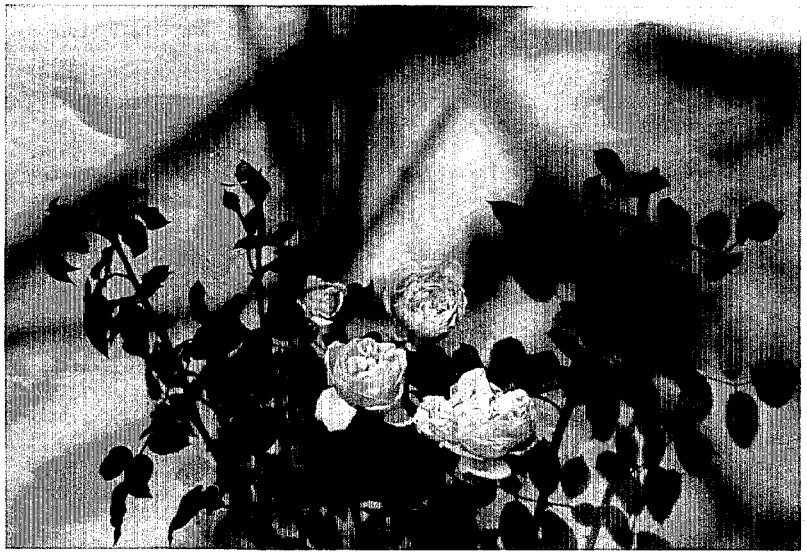

* * * * *